US011246984B2

(12) United States Patent
Richter et al.

(10) Patent No.: US 11,246,984 B2
(45) Date of Patent: Feb. 15, 2022

(54) VOLUME MEASURING ARRANGEMENT

(71) Applicant: Sanofi-Aventis Deutschland GMBH, Frankfurt am Main (DE)

(72) Inventors: René Richter, Dresden (DE); Robert Witt, Dresden (DE); Richard Guenther, Dresden (DE); Thomas Nagel, Dresden (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 178 days.

(21) Appl. No.: 16/345,933

(22) PCT Filed: Oct. 30, 2017

(86) PCT No.: PCT/EP2017/077773
§ 371 (c)(1),
(2) Date: Apr. 29, 2019

(87) PCT Pub. No.: WO2018/083062
PCT Pub. Date: May 11, 2018

(65) Prior Publication Data
US 2020/0061289 A1      Feb. 27, 2020

(30) Foreign Application Priority Data

Nov. 1, 2016    (EP) .................................... 16196679

(51) Int. Cl.
*A61M 5/168* (2006.01)
*A61M 5/148* (2006.01)
(Continued)

(52) U.S. Cl.
CPC ...... *A61M 5/16886* (2013.01); *A61M 5/1452* (2013.01); *A61M 5/1483* (2013.01);
(Continued)

(58) Field of Classification Search
CPC ........ A61M 2005/14513; A61M 5/145; A61M 5/14586; A61M 5/14593; A61M 5/148;
(Continued)

(56) References Cited

U.S. PATENT DOCUMENTS

| 5,421,208 A | 6/1995 | Packard et al. |
| 5,549,672 A | 8/1996 | Maddock et al. |

(Continued)

FOREIGN PATENT DOCUMENTS

| CN | 201012197 | 1/2008 |
| CN | 201221965 | 4/2009 |

(Continued)

OTHER PUBLICATIONS

International Preliminary Report on Patentability in Application No. PCT/EP2017/077773, dated May 7, 2019, 9 pages.

(Continued)

*Primary Examiner* — Quynh-Nhu H. Vu
(74) *Attorney, Agent, or Firm* — Fish & Richardson P.C.

(57) ABSTRACT

In one aspect the present disclosure refers to a measuring arrangement for measuring of a volume change of a liquid medium located inside a liquid reservoir, the measuring arrangement comprising:
  a gas tight enclosure having an interior volume containing a gas reservoir and containing the liquid reservoir, wherein the liquid reservoir is filled with a liquid medium,
  a gas inlet in flow connection with the gas reservoir and extending through a boundary of the gas tight enclosure to an exterior of the gas tight enclosure,
  an outlet connectable with the liquid reservoir and extending through the boundary of the gas tight enclosure,
  wherein the gas reservoir and the liquid reservoir are hermetically separated by an impenetrable separation wall, and (Continued)

a flow meter arranged in or across the gas inlet to measure an ingress of a gaseous medium through the inlet in response to a withdrawal of the liquid medium from the liquid reservoir through the outlet.

20 Claims, 3 Drawing Sheets

(51) Int. Cl.
  *A61M 5/155* (2006.01)
  *A61M 5/145* (2006.01)
(52) U.S. Cl.
  CPC ..... *A61M 5/155* (2013.01); *A61M 2205/3344* (2013.01); *A61M 2205/3368* (2013.01); *A61M 2205/3389* (2013.01); *A61M 2205/36* (2013.01)
(58) Field of Classification Search
  CPC .. A61M 5/1483; A61M 5/1486; A61M 5/152; A61M 5/155; A61M 5/282; A61M 5/281; A61M 5/30; A61M 2005/14268; A61M 2205/3334; A61M 2205/3344; A61M 5/14; A61M 5/168; A61M 5/16886; A61M 5/2053
  See application file for complete search history.

(56) References Cited

U.S. PATENT DOCUMENTS

| | | | | |
|---|---|---|---|---|
| 5,605,545 | A * | 2/1997 | Nowosielski | A61M 3/0258 604/118 |
| 5,997,501 | A * | 12/1999 | Gross | A61M 5/14248 604/65 |
| 6,629,954 | B1 * | 10/2003 | Heruth | A61M 5/148 604/131 |
| 7,008,403 | B1 | 3/2006 | Mallett et al. | |
| 8,905,970 | B2 * | 12/2014 | Bates | A61M 5/155 604/131 |
| 9,044,545 | B2 * | 6/2015 | Hagg | A61B 17/00234 |
| 2010/0008795 | A1 | 1/2010 | DiPerna | |
| 2011/0202032 | A1 * | 8/2011 | Shih | A61M 5/14276 604/500 |
| 2012/0053571 | A1 * | 3/2012 | Petri | A61M 5/1483 604/891.1 |
| 2012/0209249 | A1 * | 8/2012 | Basso | A61M 5/282 604/506 |
| 2012/0302945 | A1 | 11/2012 | Hedmann et al. | |
| 2014/0276409 | A1 | 9/2014 | Rosinko et al. | |
| 2016/0206811 | A1 * | 7/2016 | Shih | A61M 5/14276 |

FOREIGN PATENT DOCUMENTS

| | | |
|---|---|---|
| CN | 102143775 | 8/2011 |
| CN | 103443610 | 12/2013 |
| CN | 103736165 | 4/2014 |
| CN | 104487112 | 4/2015 |
| CN | 104582762 | 4/2015 |
| CN | 105163776 | 12/2015 |
| CN | 105600190 | 5/2016 |
| DE | 4220831 | 4/1994 |
| JP | 2015-505258 | 2/2015 |
| WO | WO 2007/092618 | 8/2007 |
| WO | WO 2010/046728 | 4/2010 |
| WO | WO 2010/146149 | 12/2010 |
| WO | WO 2013/096713 | 6/2013 |
| WO | WO 2014/005953 | 1/2014 |
| WO | WO 2014/123816 | 8/2014 |
| WO | WO 2014/158627 | 10/2014 |
| WO | WO 2015/048093 | 4/2015 |

OTHER PUBLICATIONS

International Search Report and Written Opinion in Application No. PCT/EP2017/077773, dated Jan. 15, 2018, 13 pages.

* cited by examiner

VOLUME MEASURING ARRANGEMENT

CROSS REFERENCE TO RELATED APPLICATIONS

The present application is the national stage entry of International Patent Application No. PCT/EP2017/077773, filed on Oct. 30, 2017, and claims priority to Application No. EP 16196679.1, filed on Nov. 1, 2016, the disclosures of which are incorporated herein by reference.

TECHNICAL FIELD

The present disclosure relates to the field of measurement devices and measurement methods, in particular to a measurement arrangement and to a respective method configured to measure a volume change of a liquid medium that is located inside a reservoir. In another aspect the disclosure relates to a drug delivery device equipped with such a measuring arrangement. The present disclosure further relates to a method of measuring a volume change of a liquid medium inside a reservoir.

BACKGROUND

Syringe systems or infusion systems are typically used for parenteral administering of liquid drugs or medicaments. Especially for patients suffering a chronic disease a regular and repeated delivery of a liquid medicament is of importance. Liquid medicaments commonly delivered via injection or via intravenous infusion. For various types of medicament delivery there exist particular drug delivery devices, such as injectors or infusion pumps. With such devices the medicament itself is typically stored and provided in a separate container. With syringe type injection devices the liquid medicament is for instance provided in a cartridge having a tubular-shaped barrel which is sealed at one longitudinal end by a pierceable septum and which is sealed at the opposite longitudinal end by means of a piston or stopper which is slidably displaceable inside the barrel.

By means of a suitable drive mechanism, typically including an advancing piston rod, the piston or stopper of the cartridge is displaceable towards a distal direction so as to expel a predefined amount of the liquid medicament from the cartridge. For this the the pierceable septum is typically pierced and penetrated by a hollow injection needle.

Other medicament delivery systems and devices, such as infusion pumps make use of a tubing in fluid communication with e.g. a flexible container or flexible reservoir containing the liquid medicament. A pump, such as a peristaltic pump may feed a well-defined amount of the medicament by way of suction. Suction pump-based drug delivery devices require a complete flushing of the tubing that extends between the medicament container and an outlet end of the tubing, which may be in direct fluid communication with biological tissue that should be subject to medicament delivery. For a proper operation medicament delivery systems and keeping track of an actual medicament delivery it is desirable to quantitatively measure the amount of medicament or a flow rate of the medicament that is actually dispensed. It is also desirable to monitor and to log the process of medicament delivery so as to record a dosing history.

It is therefore an aim to provide a measuring arrangement for measuring of a volume occupied by a liquid medium inside a reservoir. The measuring arrangement should be particularly configured and suitable for measuring of a volume change of the liquid medium and to provide a differential measurement of the volume occupied by the liquid medium. The measuring arrangement should be rather easy and straight forward to implement. It should be implementable in a space saving and cost-efficient way. The measuring arrangement should be universally applicable for different types of reservoirs configured to contain and to enclose a liquid medium or a liquid substance, such as a liquid medicament.

The measuring arrangement should be further combinable with delivery devices such as drug delivery devices, e.g. with infusion pumps, syringe-type injection devices or syringe-type infusion devices. The measuring arrangement should be implementable into such devices. The measuring arrangement should further provide a precise and reliable measurement of a volume change of a liquid medium at any time prior to or during a process of medicament delivery. Hence in some aspects, a method of measuring a volume change of a liquid medium located inside a reservoir is provided. The volume change should be measurable without getting in contact with the liquid medium.

SUMMARY

In one aspect a measuring arrangement for measuring of a volume change of a volume occupied by a liquid medium inside a reservoir is provided. The measuring arrangement comprises a gas-tight enclosure having an interior volume. The interior volume contains a gas reservoir and further contains a liquid reservoir, wherein the liquid reservoir is filled with the liquid medium. The gas reservoir is filled with a gaseous medium. Typically, the gas reservoir is entirely filled with the gaseous medium and the liquid reservoir is entirely filled with the liquid medium, such as a liquid drug or liquid medicament. The measuring arrangement further comprises a gas inlet in flow connection with the gas reservoir. The gas inlet extends through a boundary of the enclosure to an exterior of the gas tight enclosure.

There is further provided an outlet connectable to the liquid reservoir or being connected to the liquid medicament reservoir. The outlet extends through the boundary of the enclosure. Typically, the outlet also extends to an exterior of the gas tight enclosure. Since the gas inlet is in direct flow connection with the gas reservoir and to an exterior the gas inlet is particularly configured and suitable for ingress of a gaseous medium into the gas reservoir. Contrary to that, the outlet connectable to or connected to the liquid reservoir is exclusively configured and adapted to provide a flow connection for the liquid medium to escape from the interior volume and hence from the liquid reservoir. In other words, the liquid medium contained inside the liquid reservoir may escape from the liquid reservoir exclusively via the outlet.

The gas reservoir and the liquid reservoir are hermetically separated by an impenetrable separation wall. The gas reservoir and the liquid reservoir may be in direct contact to each other via the impenetrable separation wall. The separation wall is impenetrable for the gaseous medium of the gas reservoir as well as for the liquid medium contained in the liquid reservoir.

The measuring arrangement further comprises a flow meter arranged in or arranged across the gas inlet to measure a quantity of ingress of a gaseous medium through the inlet in response to a withdrawal of the liquid medium from the liquid reservoir and through the outlet. Typically, withdrawal of the liquid medium from the liquid reservoir leads to a deformation and/or to a displacement of the impenetrable separation wall. As a portion, e.g. a well-defined quantity or a dose of the liquid medium is withdrawn from the liquid reservoir the volume of the liquid reservoir decreases at the benefit of the gas reservoir. In other words, the amount of volume decrease of the liquid reservoir is substantially identical to an increase of the volume increase of the gas reservoir.

Any liquid withdrawal-induced volume change of the liquid reservoir leads to a respective increase of the volume of the gas reservoir since the interior volume of the gas-tight enclosure is substantially fixed and constant. In typical configurations the interior volume of the gas-tight enclosure is identical to the total volume occupied by the gas reservoir, the liquid reservoir and the impenetrable separation wall. Any increase or decrease of one of the liquid reservoir and the gas reservoir leads to a respective decrease or increase of the other one of the liquid reservoir and the gas reservoir.

Since the gas reservoir is in flow connection with the exterior via the inlet and since the liquid reservoir is in flow connection with the outlet a withdrawal of the liquid medium from the liquid reservoir leads to a displacement or deformation of the separation wall since the gas reservoir is in flow connection with the exterior or with atmospheric pressure via the inlet. A movement, displacement or deformation of the separation wall is a consequence of a pressure equalization or pressure balance automatically arising in response to a withdrawal of a quantity of the liquid medium from the liquid reservoir.

By arranging the flow meter across or in the gas inlet a quantity of the gaseous medium entering or leaving the gas-tight enclosure in response to a displacement or deformation of the separation wall can be measured. The volume of the quantity of the gaseous medium entering or leaving the gas reservoir through the gas inlet is substantially identical to the volume of the quantity of the liquid medium that enters the liquid reservoir or that is actually withdrawn from the liquid reservoir. Measuring of a quantity of ingress of the gaseous medium is therefore directly indicative of the volume change of the liquid medium contained in the liquid reservoir. In this way a volume change of the liquid medium inside the liquid reservoir can be determined without getting in contact with the liquid medium. Due to a permanent pressure balance between the gas reservoir and the exterior the ingress of the gaseous medium directly reflects the volume change of the liquid medium inside the liquid reservoir.

When the flow meter is configured to measure a quantity of a gas streaming through the gas inlet in both directions, not only ingress but also outflow of an amount of a gas can be quantitatively measured. In this way also a volume increase of the liquid reservoir leading to a size reduction of the gas reservoir could be measured.

In either way not only a rather precise but also a rather direct and immediate measurement of a volume change may take place. Since the flow meter does not get in contact with the liquid medium or with the liquid reservoir rather precise and high quality flow meters may be used for the measuring arrangement. Assuming a disposable liquid reservoir the measuring arrangement may be used repeatedly for a series of liquid reservoirs arrangeable inside the interior volume of the gas-tight enclosure.

The measuring arrangement is of particular use for liquid reservoirs that have a rather complex or non-constant shape, e.g. a rather flexible shape making a conventional volumetric measurement rather difficult. Measuring of a volume change of the liquid reservoir by measuring an ingress of a quantity of a gaseous medium in response to a volume change of the liquid reservoir is universally applicable for arbitrarily-shaped liquid reservoirs as long as the gas-tight enclosure provides a constant shape and a constant interior volume and as long as the liquid reservoir is entirely arranged inside the interior volume of the gas-tight enclosure.

In an embodiment the boundary of the enclosure comprises a rigid structure. The boundary, e.g. sidewalls or end walls of the boundary are substantially fixed, non-moveable and rigidly fastened with respect to each other. The boundary, its sidewall or sidewalls and its end wall or end walls is or are of non-flexible and non-deformable type. In this way it is provided that the interior volume enclosed by the gas-tight enclosure and formed by its boundary remains constant especially when a quantity of the liquid medium is withdrawn from the liquid reservoir. With a rigid structure of the boundary of the gas-tight enclosure it is somehow guaranteed, that a volume change of the liquid reservoir equally reflects in a volume change of the gas reservoir.

In another embodiment the liquid reservoir is formed by a flexible bag filled with the liquid medium. Typically, the liquid reservoir is completely sealed and forms an interior volume, which is completely confined by the sidewalls of a flexible bag. The separation wall between the liquid reservoir and the gas reservoir is then formed by the flexible bag. The liquid reservoir is typically entirely filled with the liquid medium, such as with a liquid medicament. The liquid reservoir is typically void of gas- or air bubbles. When formed or provided as a flexible bag the liquid reservoir is entirely contained and arranged inside the gas tight enclosure. Only the outlet, e.g. in form of a tubing that is flow connectable or which is flow or fluid connection with the interior of the liquid reservoir extends through the enclosure.

When arranged inside the enclosure the flexible bag forms the separation wall between the gas reservoir and the liquid reservoir. The liquid reservoir is entirely confined by flexible sidewall portions of the flexible bag. The flexible bag may even be entirely surrounded by the gas reservoir. The volumetric measurement can be conducted totally independent and irrespective of a specific geometric shape of the liquid reservoir and its flexible bag as long as the flexible bag is entirely filled with the liquid medium and as long as the flexible bag is in direct contact with the gas reservoir inside the container via the separation wall.

In another embodiment the liquid reservoir is formed in part by the enclosure. Here, the liquid reservoir is separated from the gas reservoir by a flexible membrane. The flexible membrane may separate the interior volume of the enclosure into a liquid chamber and into a gas chamber of the interior volume. The shape and position of the flexible membrane may change in accordance with the delivery or withdrawal of the liquid medicament from the liquid reservoir. Typically and in an initial configuration at least an outer border of the flexible membrane may be fixed to an inside facing sidewall portion of the enclosure. As the liquid reservoir constantly empties a middle portion of the flexible membrane spaced apart from the outer border region thereof may be subject to a deformation towards the outlet of the enclosure. The flexible membrane is just another embodiment of the impenetrable separation wall separating the liquid reservoir and the gas reservoir.

Arranging of a flexible membrane inside the enclosure may be rather cost efficient and easy to manufacture. Here, the enclosure or at least a part thereof with the flexible membrane may be designed and configured as a disposable unit that is intended to be discarded in its entirety once the liquid medium has been withdrawn or expelled therefrom.

In embodiments with a flexible bag forming the liquid reservoir the flexible bag may be designed and configured as a disposable unit that is intended to be discarded in its entirety once the liquid medium has been withdrawn or expelled therefrom.

In another embodiment the liquid reservoir is formed in part by the enclosure. Here, the separation wall comprises a piston slidably arranged in a longitudinally extending guiding section of the enclosure. With this embodiment the impenetrable separation wall is formed by the piston and coincides with the piston. The piston itself may be flexible or rigid. As a withdrawal of the liquid medium takes place, the permanent pressure balance of the gas reservoir with the exterior provides ingress of a respective amount of the gaseous medium which allows and supports a respective displacement of the piston along the guiding section of the enclosure, typically towards the outlet. In typical embodiments the piston acts and behaves as a separation wall between the liquid reservoir and the gas reservoir. It is typically in sealing engagement with the boundary of the gas-tight enclosure. Typically, the piston is in gas-tight engagement with the longitudinally extending guiding section. Here, the guiding section may form at least a portion of the boundary of the gas-tight enclosure.

In this embodiment the boundary of the gas-tight enclosure constitutes to both, the liquid reservoir as well as to the gas reservoir. Liquid reservoir and gas reservoir are then just separated by the displaceable piston. Typically, the gas inlet and the outlet of the gas-tight enclosure are located on opposite sides of the piston. Also here, the liquid reservoir separated from the gas reservoir only via the piston is void of any gas enclosures or gas bubbles and vice versa. The gas reservoir is typically void of a liquid medium.

The measuring arrangement is hence universally applicable to a large variety of differently shaped gas-tight enclosures. When comprising a piston as a separation wall the gas-tight enclosure may comprise a syringe-type and tubular-shaped cartridge divided into a gas reservoir and a liquid reservoir. In other embodiments the gas-tight enclosure is just an enclosure with a constant interior volume and having a flexible bag located therein, thus forming the liquid reservoir filled with the liquid medium.

In an embodiment a flow restrictor is arranged in or across the gas inlet between an inlet end of the gas inlet and the flow meter. By means of a flow restrictor, ingress of the gaseous medium through the inlet can be controlled and decelerated. In this way, the precision of the measurement of the quantity of ingress of the gaseous medium can be improved. A flow or flux of the ingress of the gaseous medium through the inlet can be better controlled by means of the flow restrictor. The flow restrictor may comprise some type of a gas penetrable membrane providing a well-defined flow resistance for the influx of the gaseous medium through the gas inlet.

In a further embodiment the flow meter comprises a differential pressure sensor. For instance, the pressure sensor may be implemented in conjunction with the Venturi effect to measure a flow. A differential pressure is hence measured between two segments of a Venturi tube that have a different aperture. The pressure difference between the two segments is directly proportional to the flow rate through the Venturi tube. Such a Venturi tube may be arranged inside and/or across the gas inlet typically downstream of the flow restrictor but upstream of the gas reservoir.

Alternative to a Venturi-based flow measurement the flow meter may comprise a rather thin electronic membrane arranged across the gas inlet so as to expose the electronic membrane in the stream of influx of the gaseous medium. The membrane may have a thin film temperature sensor printed on the upstream side and another thin film temperature sensor on the downstream side. A heater may be integrated in the center of the membrane which maintains a constant temperature similar to the so-called hot-wire approach. Without any airflow, the temperature profile across the membrane is uniform. When the gaseous medium flows across the membrane, the upstream side cools differently from the downstream side. The difference between the upstream and downstream temperature indicates the mass airflow. Nowadays technological progress allows this kind of sensor to be manufactured on a microscopic scale as a microsensor using microelectromechanical system technologies.

In general, the flow meter is not restricted to the above mentioned technical solutions for a quantitative measurement of a flow of a gaseous medium. Generally, any type of flow meter configured to precisely determine a quantity of a flow of a gaseous medium through the inlet is implementable with the present measuring arrangement.

In a further embodiment the measuring arrangement comprises a controller connected to the flow meter to calculate the volume change of the liquid reservoir on the basis of signals received from the flow meter. The controller typically comprises a microprocessor to process and to analyze electric signals obtainable from the flow meter. Signal analysis or signal processing of signals provided by the flow meter are directly indicative of the quantity and amount of the gaseous medium entering the gas reservoir during a pressure balance of gas reservoir and liquid reservoir that is induced by a withdrawal of the liquid medium from the liquid reservoir. The controller is configured to determine a volume change of the gas reservoir, which is identical to a corresponding and complementary volume change of the liquid reservoir.

In another embodiment the enclosure comprises a first part and a second part that are detachably connectable to form the interior volume. The first part and the second part are also sealingly engageable in a gas-tight and fluid-tight manner. The separation wall separating the liquid reservoir and the gas reservoir may form an outer boundary of the first part or of the second part of the enclosure. When the liquid reservoir is implemented as a flexible bag it may be at least partly located inside one of the first or second parts of the gas-tight enclosure.

Separation of the gas-tight enclosure into at least a first part and a second part enables a hybrid design of the gas-tight enclosure. For instance the first part may be configured as a reusable component of the gas-tight enclosure and the second part may be configured as a disposable component of the gas-tight enclosure. High quality and rather durable as well as expensive components of the measuring arrangement may be fixedly attached to the first part whereas rather low cost components and/or components or portions that get in direct contact with the liquid medium may be provided in or may be attached to the second part, configured as a disposable component of the gas-tight enclosure. Disposable components are configured and intended for a complete discarding after usage contrary to reusable components, that may be used repeatedly and for a long term.

The separation of the gas-tight enclosure into at least a first part and a second part also enables a direct integration of the measuring arrangement into a drug delivery device. At least one of the first part and the second part of the gas-tight enclosure may form or may coincide with a housing or with a portion or part of a housing of a drug delivery device. In this way, any empty space inside the housing of a drug delivery device and sealed gas-tight to the exterior may act and behave as the gas reservoir of a measuring arrangement as described above.

In another embodiment the gas inlet is connected to the first part of the enclosure. Alternatively, the gas inlet is integrated into the first part. Also, the flow meter is connected to the first part. It is still arranged in or across the gas inlet. With this implementation the first part and the flow meter as well as the gas inlet are configured as reusable components of the measuring arrangement. Here, the second part of the gas-tight enclosure may be configured as a disposable component. Depending on the type of liquid reservoir it is also conceivable, that the second part of the gas-tight enclosure is reusable and can be repeatedly sealingly attached to the first part so as to form the gas-tight enclosure.

Providing the flow meter in or at the first part of the gas-tight enclosure enables the use of a high quality flow meter repeatedly usable with a series of liquid reservoirs, typically configured and designed as a disposable part.

Rather durable and high quality and hence cost intensive components of the measuring arrangement are therefore intended for multiple uses, thus reducing the total cost for implementing the measuring arrangement.

In an embodiment the liquid reservoir is filled with a liquid medicament. In further embodiments the liquid reservoir is arranged in the second part or the liquid reservoir is formed in part by the second part of the gas-tight enclosure. The liquid reservoir may be pre-arranged inside the second part and/or may be simply attached to the second part. The liquid reservoir together with the second part may be preconfigured and may be commercially distributed in combination with each other as a replacement kit to replace an empty liquid reservoir by a new one. In the course of replacement the second part with the empty liquid reservoir is detached from the first part and a new second part with a filled liquid reservoir is attached to the first part to form the gas-tight enclosure.

Since the gas inlet and the flow meter remain attached to the reusable first part the exchange of a liquid reservoir has no consequences on the process of volumetric measurement conducted by the measuring arrangement. There is even no necessity to reset the controller after a replacement of the liquid reservoir. As the withdrawal of the liquid medium from the liquid reservoir continues the flow meter just detects a respective volumetric change of the liquid reservoir and the gas reservoir inside the gas-tight enclosure.

In another aspect a drug delivery device is provided that comprises a housing and further comprises a measuring arrangement as described above. The drug delivery device also comprises a delivery mechanism operably engageable with the liquid reservoir so as to withdraw a quantity of the liquid medium therefrom. The drug delivery device may be configured and implemented as an infusion pump or as an infusion system. Alternatively, the drug delivery device may be configured as an injection device, such as a syringe-type injection device.

In typical embodiments the above mentioned controller of the measuring arrangement may coincide with and may be provided by an electronic controller of the drug delivery device. Hence, the measuring arrangement as described above may be entirely integrated into the drug delivery device. Implementing of the measuring arrangement into a drug delivery device enables a precise volumetric measurement of a volume change of a liquid reservoir filled with a liquid medium, in particular filled with a liquid medicament. During medicament delivery the ingress of a gaseous medium into the gas reservoir as a consequence of a withdrawal of the liquid medium from the liquid reservoir can be permanently detected by means of the flow meter and can be hence monitored and logged by the controller of the measuring arrangement and/or by the controller of the drug delivery device.

According to a further embodiment the delivery mechanism comprises a suction pump flow connectable with the outlet or with the liquid reservoir to withdraw the liquid medium from the liquid reservoir. The suction pump may be in flow- or fluid communication with the outlet and may be hence in fluid communication with the liquid reservoir. The suction pump may be implemented as a peristaltic pump or as a piston pump as an example. The suction pump may provide a constant or a pulsed flow of the liquid medium from the liquid reservoir. The suction pump leads to a negative pressure in the liquid reservoir. Due to the flexible, deformable or displaceable separation wall the liquid reservoir is in pressure balance with the gas reservoir. Consequently, and as a response to a withdrawal of a quantity of the liquid medium from the liquid reservoir the configuration or position of the separation wall changes so as to modify the volume of the gas reservoir. This leads to the measurable ingress of the gaseous medium into the gas reservoir, which is actually measured by the flow meter.

With other embodiments the delivery mechanism comprises a piston-type configuration by way of which a quantity of the liquid medium is either sucked out of the liquid reservoir or by way of which the liquid medium is expelled from the liquid reservoir, e.g. by a mechanically induced displacement of the separation wall, e.g. by the displacement of a piston slidably engaged with a guiding section of the gas-tight enclosure.

In another embodiment of the drug delivery device the enclosure comprises at least a first part and a second part. At least one of the first part and the second part of the gas-tight enclosure forms at least a portion of the housing of the drug delivery device. In this way, an empty space inside the housing may serve as the gas reservoir. It is even conceivable, that the housing of the drug delivery device coincides with the gas-tight enclosure of the measuring arrangement. Here, a first housing portion may coincide with the first part of the gas-tight enclosure and a second housing portion may coincide with the second part of the gas-tight enclosure. Then, first and second housing portions are releasably connectable in a gas-tight manner. The first part and the second part may be detachably connectable to form the interior volume.

With this embodiment it is conceivable, that the gas-tight enclosure of the measuring arrangement is exclusively formed by the housing of the drug delivery device. Providing of a separate gas-tight enclosure inside the housing of a drug delivery device therefore becomes superfluous. This provides and enables a reduction of the total number of components for implementing the drug delivery device and the measuring arrangement.

In another aspect a method of measuring a volume change of a liquid medium located inside a liquid reservoir and arranged inside a gas-tight enclosure is provided. Here, the enclosure further contains a gas reservoir hermetically separated from the liquid reservoir by an impenetrable separation wall. The method of measuring of the volume change comprises the steps of withdrawing of a portion of the liquid medium from the liquid reservoir thereby inducing a volume change of the liquid reservoir leading to a movement or to a deformation of the separation wall, thus enlarging the volume of the gas reservoir. Thereafter and in a further step a quantity of ingress of a gaseous medium into the gas reservoir through a gas inlet in flow connection with the gas reservoir and extending through a boundary of the enclosure to an exterior is measured.

Based on this measurement and in a further step the quantity of the volume change of the liquid reservoir and hence the volume change of the liquid medium contained therein is derived on the basis of the measured flow of the gaseous medium into the gas reservoir or out of the gas reservoir.

Typically, the volume change, i.e. the volume reduction of the liquid medium in the liquid reservoir is substantially identical to the ingress of the volume of the gaseous medium into the gas reservoir as soon as a pressure balance between the liquid reservoir, the gas reservoir and the exterior has been reached. In this way a volume change of the liquid medium can be precisely measured without the necessity to get in direct contact with the liquid medium. Hence, a risk of contamination of the liquid medium can be reduced to a minimum.

The method of measuring of the volume change of the liquid medium is typically conducted by a measuring arrangement and/or by a drug delivery device as described above. It is to be noted that any features, benefits and effects obtainable with the measuring arrangement and/or with the drug delivery device are equally valid for the above mentioned method of measuring of a volume change of the liquid medium; and vice versa.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group-Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4 (1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4 (1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp (O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2) 25, Asp28] Exendin-4(S1-39)-(Lys)6-NH2, H-Asn-(Glu)5-des Pro36, Pro37, Pro38 [Met(O)14, Trp (O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present invention without departing from the spirit and scope of the invention as defined in the appended claims. Further, it is to be noted, that any reference numerals used in the appended claims are not to be construed as limiting the scope of the invention.

BRIEF DESCRIPTION OF THE FIGURES

In the following, embodiments of the present invention will be described by making reference to the drawings, in which.

DETAILED DESCRIPTION

Figure 1:
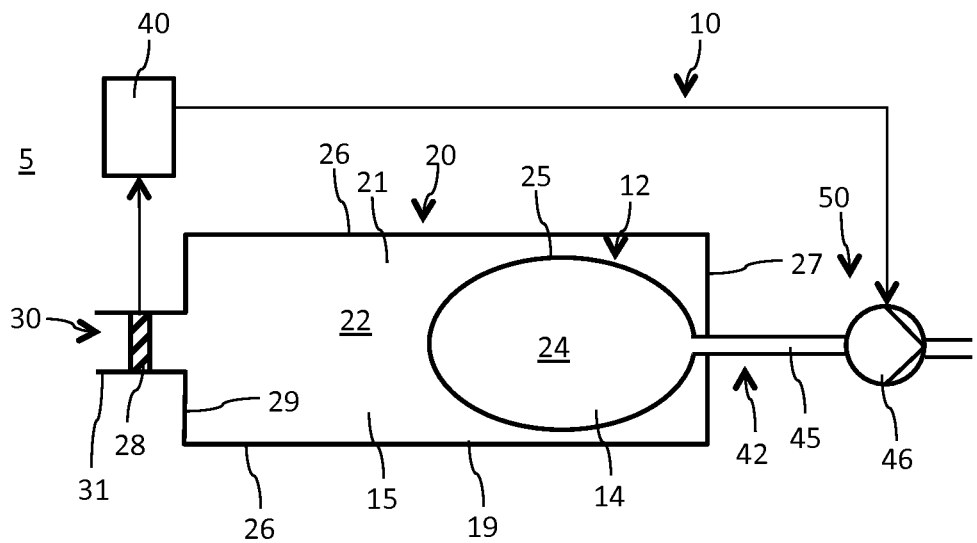
FIG. 1 is a schematic block diagram of the measuring arrangement.

In FIG. 1 an embodiment of the measuring arrangement 10 is schematically illustrated. The measuring arrangement 10 comprises a gas-tight enclosure 20 confining an interior volume 21. Inside the enclosure 20 there is located a gas reservoir 22 filled with a gaseous medium 15. Inside the interior volume 21 there is further provided and contained a liquid reservoir 24 filled with a liquid medium 14. The gas reservoir 22 and the liquid reservoir 24 are hermetically separated by means of an impenetrable separation wall 25. The separation wall 25 is impenetrable with regard to the gaseous medium 15 and with regard to the liquid medium 14. In the embodiment of FIG. 1 the separation wall 25 is flexible and/or deformable. The separation wall 25 is formed by a flexible bag 12 in which the liquid medium 14, e.g. a liquid medicament is stored.

Typically, the liquid medium 14 entirely fills the interior of the liquid reservoir 24. The liquid reservoir 24 is void of any air or gas bubbles. The liquid reservoir 24 is entirely located inside the interior volume 21 of the enclosure 20. The enclosure 20 has a rigid boundary 19. As illustrated in FIG. 1 the boundary 19 comprises a rigid sidewall 26 as well as rigid end walls 27, 29. Inside the gas reservoir 22 and hence inside the interior volume 21 but outside the liquid reservoir 24 there is located a gas inlet 30 in flow connection with the gas reservoir 22 and extending through the boundary 19 of the enclosure 20 to an exterior 5. The exterior 5 may be the outer environment of the measuring arrangement 10.

The exterior 5 may be subject to atmospheric pressure. The measuring arrangement 10 further comprises an outlet 42 that is connected to the liquid reservoir 24. The outlet 42 is configured as a tubing 45 in flow connection or fluid connection with the interior of the liquid reservoir 24. As further illustrated in FIG. 1 the outlet 42 and hence the tubing 45 is in flow connection with a suction pump 46 by way of which a quantity of the liquid medium 14 can be extracted or withdrawn from the liquid reservoir 24. Across or inside the gas inlet 30 there is provided a flow meter 28 that is configured to measure a quantity of ingress of a gaseous medium 15 through the inlet 30 in response to a withdrawal of the liquid medium 14 from the liquid reservoir 24.

Typically and since the liquid reservoir 24 and the gas reservoir 22 are in a pressure balance any deformation of the flexible bag 12 in response to a withdrawal of the liquid medium 14 therefrom leads to an increase of the volume of the gas reservoir 22. Due to the pressure balance between the gas reservoir 22 and the liquid reservoir 24 and due to the flow connection of the gas reservoir 22 to the exterior 5 a quantity of a gaseous medium flows into the gas reservoir 22. The flow meter 28 is configured to measure the quantity of ingress of the gaseous medium, e.g. of ambient air. The measured ingress of the quantity of the gaseous medium is hence a direct indication of the volume change of the liquid reservoir 24 and hence of the amount and of the volume of the liquid medium 14 withdrawn from the liquid reservoir 24.

There is further illustrated a controller 40 that is connected to the flow meter 28. The controller 40 is configured to calculate the volume change of the liquid reservoir 24 on the basis of the measured ingress of the gaseous medium 15 into the gas reservoir 22 that takes place in response to a volume change of the liquid reservoir 24.

Optionally the controller 40 may be also connected to the suction pump 46. Typically, the controller 40 may trigger or may activate the suction pump 46. If in response to the activation of the suction pump 46 the controller will not receive any measurable or reasonable signals from the flow meter 28 this is an indication that the measuring arrangement 10 or a drug delivery device 100 is subject to malfunction. If a control signal submitted from the controller 40 to the suction pump 46 does not match with a measurement signal obtainable from the flow meter 28 the fluid path may be for instance occluded. Implementation of the flow meter 28 in or across a gas inlet 30 and measuring a quantity of ingress of a gaseous medium provides a direct indication of an actual volume change of the liquid reservoir 24.

Figure 2:
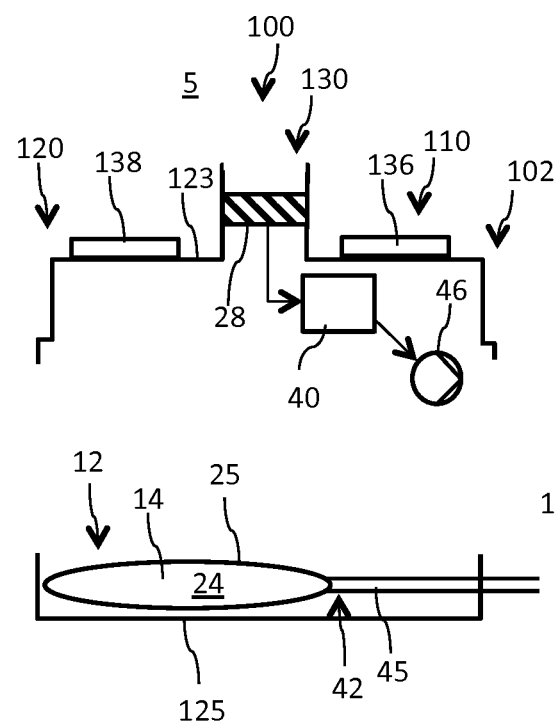
FIG. 2 shows a drug delivery device with a first and with a second housing component in a detached configuration.
Figure 3:
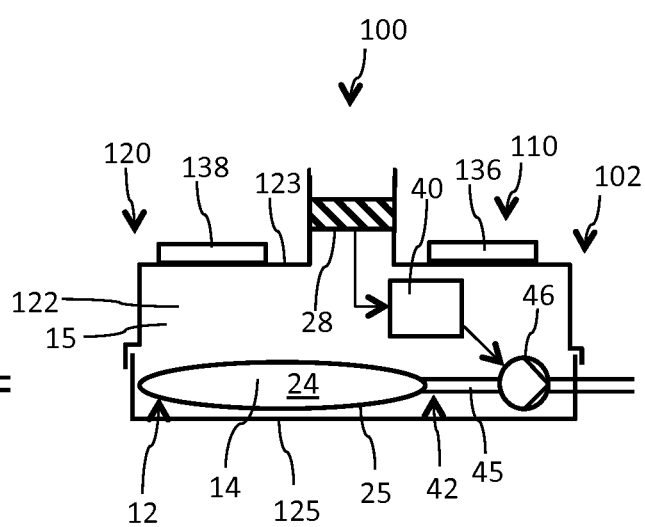
FIG. 3 shows the drug delivery device according to FIG. 2 in an assembled configuration.

In FIGS. 2 and 3 another embodiment of the measuring arrangement 110 is illustrated. Here, the measuring arrangement 110 is integrated into a drug delivery device 100. The drug delivery device 100 comprises a housing 102. The measuring arrangement 110 included and integrated into the drug delivery device 100 comprises an enclosure 110 that may coincide with the housing 102 or that may form the housing 102 of the drug delivery device 100. In other embodiments the enclosure 120 may be arranged inside the housing 102 or may only form part of the housing 102.

The enclosure 120 comprises a first part 123 and a second part 125. As shown in FIGS. 2 and 3 the first and the second parts 123, 125 are releasably and detachably connectable so as to form a gas-tight enclosure 120 or to form a gas-tight and closed housing 102 of the drug delivery device 100. The enclosure 120 formed by the first part 123 and the second part 125 comprises an interior volume 121. In the embodiment as illustrated in FIGS. 2 and 3 the second part 125 is provided with the liquid reservoir 24 as described above and hence with a flexible bag 12 containing the liquid medium 14, e.g. the liquid medicament.

When the two parts 123, 125 are assembled together in a gas-tight way the liquid reservoir 24 is entirely surrounded by the gas reservoir 122 which is formed by empty spaces inside the housing 102 of the drug delivery device 100. In the illustrated embodiment the liquid reservoir 24 may comprise a rather flat and flexible bag 12 thus allowing a rather compact and flat design of the first and the second parts 123, 125. In this way a rather compact housing 102 and a rather miniaturized drug delivery device 100 can be provided. Here, the first part 123, illustrated as an upper part of the housing 102 is equipped with the flow meter 28 arranged across the gas inlet 130.

Similar as described above in connection with the embodiment of FIG. 1 the flow meter 28 is connected to a controller 40 and the controller 40 is connected to a suction pump 46. At least one or both of the controller 40 and the suction pump 46 are also attached and assembled to the first part 123. The first part 123 may be configured as a reusable part of the measuring arrangement 110 or of the drug delivery device 100 whereas the second part 125 equipped with the liquid reservoir 24 and optionally with a tubing 45 may be configured as a disposable part. When assembled together and as shown in FIG. 3 the suction pump 46, e.g. configured as a peristaltic pump may engage with a flexible tubing 45 in flow connection with the interior of the liquid reservoir 24.

Withdrawal of the liquid medium 14 from the liquid reservoir 24 leads to a continuous or stepwise decrease of the volume of the flexible bag 12 thus increasing the available volume of the gas reservoir 122. As a consequence gaseous medium 15 is sucked into the gas reservoir from the exterior 5 and through the gas inlet 130. By measuring the amount of ingress of the gaseous medium 15 by means of the flow meter 28 the volume change of the liquid reservoir and hence the volume of the liquid medium 14 withdrawn from the liquid reservoir 24 can be precisely determined.

Typically, all reusable and rather valuable or high quality components of the drug delivery device 100 and/or of the measuring arrangement 110 are all provided inside or are attached to the first part 123. In this way the costs for manufacturing the disposable second part 125 can be decreased to a minimum.

With a one-time usable second part 125 preconfigured with the liquid reservoir 24 and typically in permanent fluid communication with the outlet 42 and/or with the tubing 45 all fluid guiding components of the measuring arrangement 110 and/or of the drug delivery device 100 that may get in direct contact with the liquid medium 14 are configured as disposable components, which after delivery of the liquid medium 14 are intended to be discarded.

The drug delivery device 100 as shown in FIGS. 2 and 3 may be further provided with a display 136 and with an actuation member 138, hence with an input unit so as to control operation of the drug delivery device 100. The display 136 may provide information to a user of the device about the medicament delivery actually taking place and/or about a dosing or delivery history. By means of the actuation member 138 a delivery process of the liquid medium can be triggered and controlled.

Figure 4:
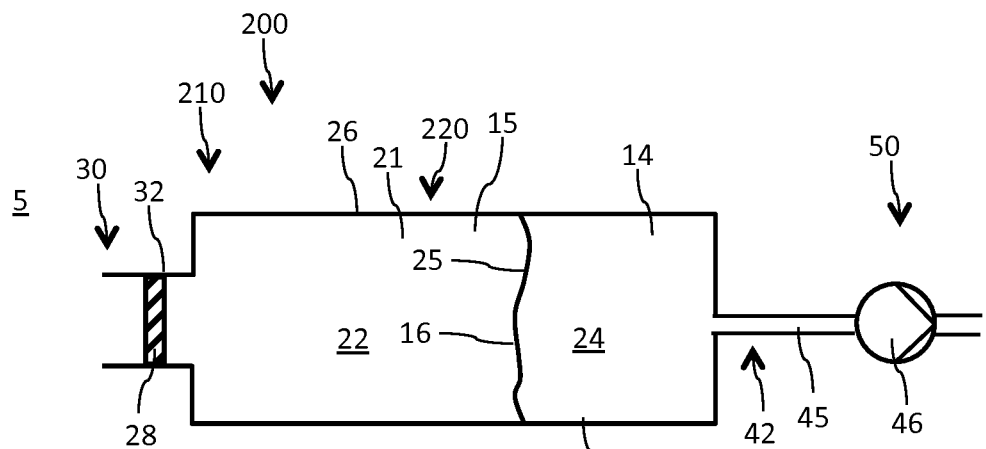
FIG. 4 is illustrative of another embodiment of the measuring arrangement with a flexible membrane separating the liquid reservoir and the gas reservoir.
Figure 5:
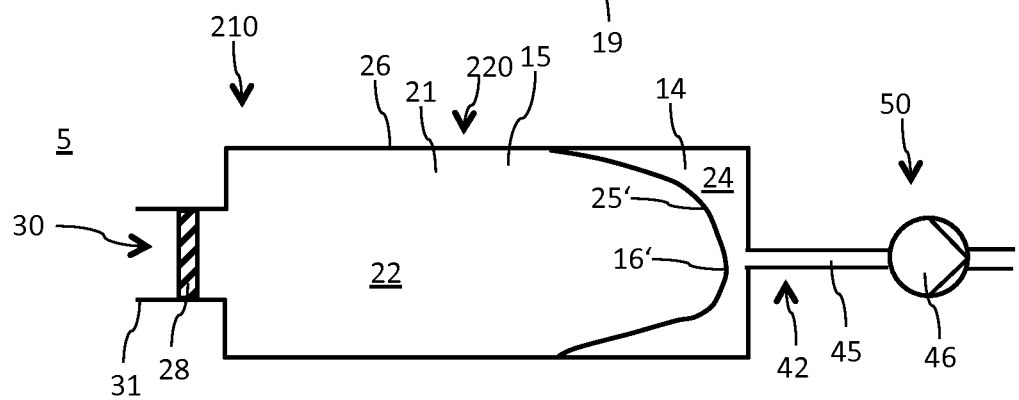
FIG. 5 shows the embodiment according to FIG. 4 after withdrawal and extraction of a quantity of the liquid medium.

In FIGS. 4 and 5 another embodiment of the measuring arrangement 210 that may represent another type of drug delivery device 200 is illustrated. The general structure and functionality of the measuring arrangement 210 is rather identical or similar to the measuring arrangement 10 as described in connection to FIG. 1. As far as not indicated otherwise identical components are denoted with identical reference numbers.

Instead of a closed flexible bag 12 the liquid reservoir 24 is now formed by a membrane 16 that is impenetrable for the gaseous medium 15 and which is also impenetrable for the liquid medium 14. As shown in an initial configuration according to FIG. 4, the membrane 16, typically implemented as a flexible membrane 16 is attached to the interior of a sidewall 26 of the gas-tight enclosure 220. The enclosure 220, its boundary 19 and hence its sidewall 26 may comprise a tubular shape. An outer circumference of the membrane 16 may be permanently and fixedly attached to the inside of the sidewall 26 of the pressure-resistant and rather rigid boundary 19 of the enclosure 20.

As apparent from a comparison of FIGS. 4 and 5 the liquid medium 14 may be subject to withdrawal when the respective drug delivery device 200 is operated, e.g. by activation of the suction pump 46. As a consequence and since the liquid reservoir 24 is hermetically sealed to the gas reservoir 22 the volume of the liquid reservoir 24 will constantly or stepwise decrease. The change of the size of the liquid reservoir 24 reflects in a deformation of the separation wall 25' and hence in a respective deformation of the flexible membrane 16'. Since the boundary 19 and hence the gas-tight enclosure 220 is of a constant volume a reduction of the volume of the liquid reservoir 24 leads to an increase of the volume of the gas reservoir 22. As a consequence and as already described above, the withdrawal of the liquid medium 14 from the liquid reservoir 24 through the tubing 45 leads to a respective ingress of a gaseous medium 15 into the gas reservoir 22. The flow meter 28 configured to measure the quantity of the gaseous medium 15 entering the interior volume 21 generates respective electrical signals that are processed by the controller 40 in a way as described above.

Figure 6:
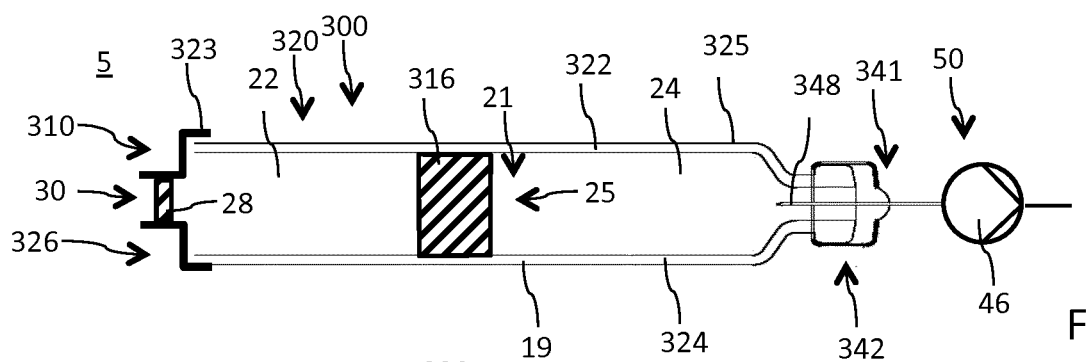
FIG. 6 is illustrative of another embodiment with a cartridge or syringe-type gas-tight enclosure in connection with a suction pump.

The further embodiment as shown in FIG. 6 is illustrative of another measuring arrangement 310 and another drug delivery device 300. Here, the gas-tight enclosure 320 comprises a tubular-shaped barrel 324 providing an elongated guiding section 322. The interior volume 21 of the barrel 324 is divided by a separation wall 25. Here, the separation wall 25 is formed by a piston 316 slidably displaceable inside the barrel 324. The piston 316 separates a liquid reservoir 24 from a gas reservoir 22. As further illustrated the liquid reservoir 24 is in flow connection with a pierceable outlet 342. The outlet 342 may comprise a pierceable septum 341 that is penetrable and pierceable by a piercing element 348, such as a cannula in flow connection with a suction pump 46. In this way and by activation of the suction pump 46 the liquid medium 14 can be withdrawn from the liquid reservoir 24.

An end section of the barrel 324 opposite to the outlet 342 is sealed by a first part 323 of the gas-tight enclosure 320. The first part 323 may form or may comprise a closure, e.g. in form of a closure cap sealingly attachable to an end section of the tubular-shaped barrel 324. Here, the barrel 324 may form a second part of the gas-tight enclosure 320. As further shown in FIG. 6 the first part 323 comprises a gas inlet 30 with a flow meter 28. Even though not illustrated the flow meter 28 is connectable or is connected to a controller 40 so as to measure and to process electric signals obtainable from the flow meter 28.

As the liquid medium 14 is withdrawn from the liquid reservoir 24, the piston 316 is subject to a sliding displacement towards the outlet 342 thereby increasing the volume of the gas reservoir 22. As a consequence and as described above this displacement of the piston 316 and hence of the separation wall 25 leads to an ingress of a respective and measurable amount of gaseous medium 15 into the gas reservoir 22.

Figure 7:
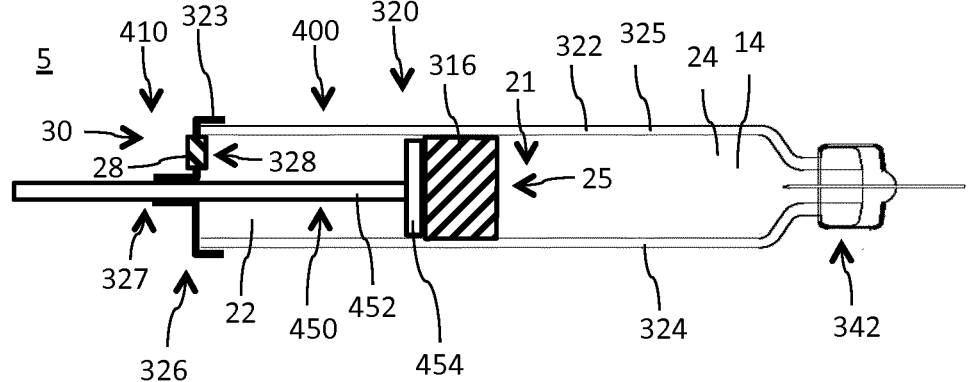
FIG. 7 is indicative of another embodiment of the measuring arrangement with a cartridge- or syringe-type gas-tight enclosure.

In FIG. 7 a further embodiment of a drug delivery device 400 in connection with a further embodiment of a measuring arrangement 410 is illustrated. The embodiment according to FIG. 7 is rather similar to the embodiment of FIG. 6 except that the withdrawal of the liquid medium 14 is not suction-based but is based on a mechanical and thrust-induced displacement of the separation wall 25. As illustrated the first part 323 of the gas-tight enclosure 320 is intersected by a delivery mechanism 450 having a displaceable piston rod 452 with a radially enlarged pressure piece 454 at an end section that is located inside the gas reservoir 22. The piston rod 452 is configured to exert a pressure to the piston 316 so as to move the piston 316 towards the outlet 342.

The first part 323 comprises an orifice 327 through which the piston rod 452 extends. Typically, the orifice 327 is sealed gas-tight to the piston rod 452 so that ingress of the gaseous medium 15 occurs exclusively through the gas inlet 30 that is provided by a further orifice 328 of the first part 323 that forms a closure 326 of an open end section of the barrel 324. The advancing motion of the piston rod 452 may be triggered and controlled by the controller 40. Alternatively the advancing motion may be manually applied.

Figure 8:
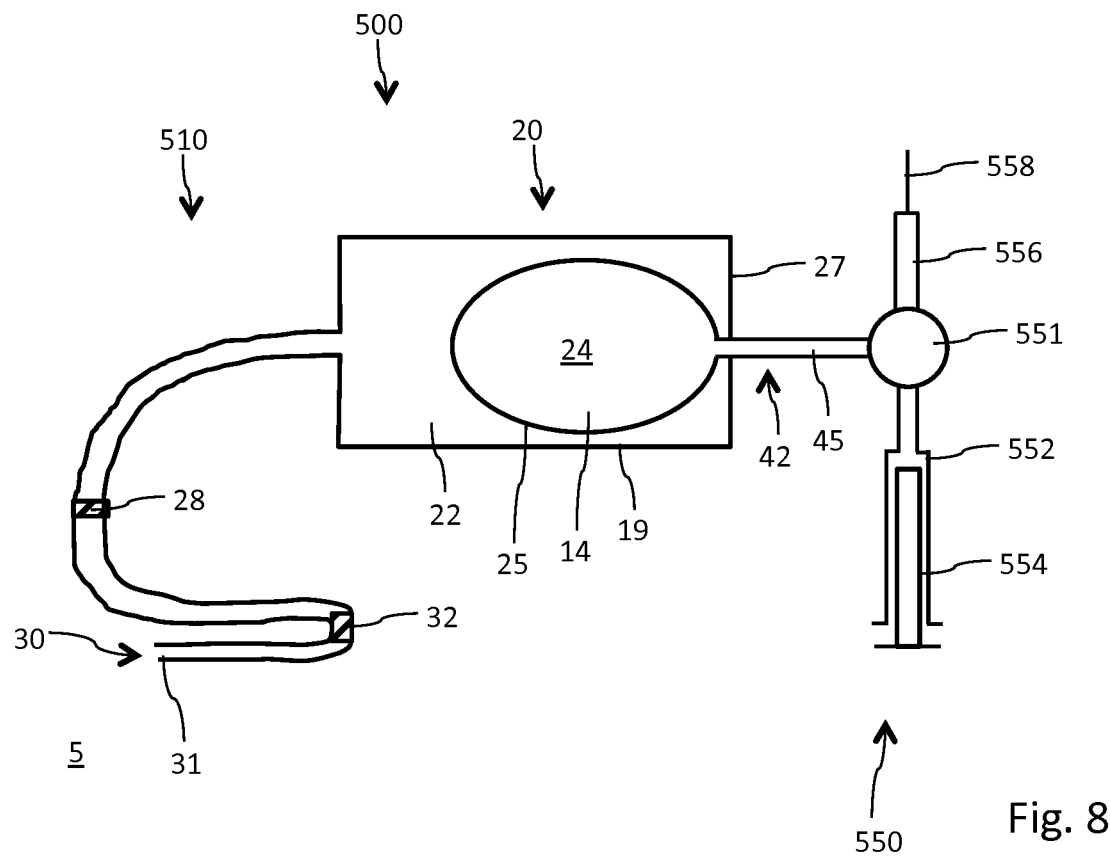
FIG. 8 shows another embodiment of the drug delivery device with a syringe-type delivery mechanism in combination with a measuring arrangement similar to the one as illustrated in FIG. 1

In FIG. 8 another embodiment of the measuring arrangement 510 in connection with a further embodiment of a drug delivery device 500 is shown. Here, the gas-tight enclosure 20 is substantially identical or rather similar to the enclosure 20 as shown in FIG. 1. But contrary to the embodiment as shown in FIG. 1 the gas inlet 30 is of elongated shape. It may comprise a flexible tube with an open inlet end 31 through which the gaseous medium can be sucked or drawn in.

Inside and across the gas inlet 30 the flow meter 28 is arranged. Between the inlet end 31 and the flow meter 28 there is further provided a flow restrictor 32. The flow restrictor 32 is located upstream of the flow meter 28 so as to homogenize and to decelerate a flux of the gaseous medium 15 entering the gas inlet 30 in response to a volume increase of the liquid reservoir 24.

For withdrawal of the liquid medium 14 from the liquid reservoir 24 the tubing 45 is connected to a switchable valve 551. One end of the valve 551 is connected to a syringe 552 comprising a displaceable piston 554. When the valve 551 is in a configuration so as to provide a flow connection between the tubing 45 and the syringe 552 an amount of the liquid medium 14 can be withdrawn from the liquid reservoir 24 and into the syringe 552. Then, the configuration of the valve 551 has to be changed so as to decouple the tubing 45 from the syringe 552 and to establish a flow connection between the syringe 552 with an injection needle 558 connected via a socket 556 to an outlet of the valve 551. The liquid medium 14 contained inside the syringe 552 can be then expelled via the injection needle 558.

The various embodiments as shown in FIGS. 1-8 disclose different types of delivery mechanisms. The delivery mechanism 50 as shown in FIGS. 1-6 is based on a suction-implemented withdrawal of the liquid medium 14, hence of a liquid medicament from the liquid reservoir 24. Typically, the delivery mechanism 50 comprises a suction pump 46. The delivery mechanism 450 as depicted in FIG. 7 is based on a mechanical displacement of the separation wall 25 and the delivery mechanism 550 as shown in FIG. 8 is based on a syringe-type and suction-based withdrawal of the liquid medium 14 from the liquid reservoir 24.

Figure 9:
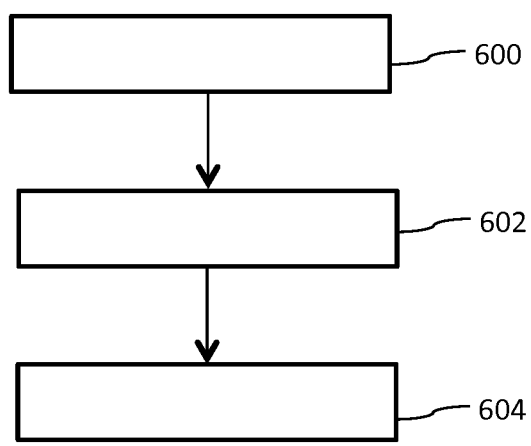
FIG. 9 is a flowchart of the method of measuring of a volume change of the liquid medium inside the liquid reservoir.

In FIG. 9 a flowchart of a method of measuring a volume change of the liquid medium 14 is given. In a first step 600 a quantity or a portion of the liquid medium 14 is withdrawn from the liquid reservoir 24. This induces a volume change of the liquid reservoir 24 leading to a movement or to a deformation of the separation wall 25. Since the total volume of the enclosure 20 is constant and since the liquid reservoir 24 and the gas reservoir 22 are pressure balanced the deformation or movement of the separation wall 25 enlarges the volume of the gas reservoir 22. In a subsequent step 602 a quantity of ingress of a gaseous medium 15 into the gas reservoir 22 through the gas inlet 30 is measured by means of the flow meter 28. Based on the measurement of the flow meter 28 and the electrical signals generated by the flow meter 28 in the subsequent step 604 the volume change of the liquid reservoir 24 and hence the volume change of the liquid medium 14 contained therein is derived and/or calculated on the basis of the signals provided by the flow meter 28 and hence on the basis of the measured ingress of the gaseous medium 15 into the gas reservoir 22.

LIST OF REFERENCE NUMBERS 5 exterior
10 measuring arrangement
14 liquid medium
15 gaseous medium
16 membrane
19 boundary
20 enclosure
21 interior volume
22 gas reservoir
24 liquid reservoir
25 separation wall
26 sidewall
27 end wall
28 flow meter
29 end wall
30 gas inlet
31 inlet end
32 flow restrictor
40 controller
42 outlet
45 tubing
46 suction pump
50 delivery mechanism
100 drug delivery device
102 housing
110 measuring arrangement 120 enclosure
123 first part
125 second part
130 gas inlet
136 display
138 actuation member
200 drug delivery device
210 measuring arrangement
220 enclosure
300 drug delivery device
310 measuring arrangement
320 enclosure
322 guiding section
323 first part
324 barrel
325 second part
326 closure
327 orifice
328 orifice
341 septum
342 outlet
348 piercing element
400 drug delivery device
410 measuring arrangement
450 delivery mechanism
452 piston rod
454 pressure piece
500 drug delivery device
510 measuring arrangement
550 delivery mechanism
551 valve
552 syringe
554 piston
556 socket
558 injection needle

The invention claimed is:

1. A measuring arrangement comprising:
a gas tight enclosure having an interior volume containing a gas reservoir and containing a liquid reservoir, wherein the liquid reservoir is filled with a liquid medium;
a gas inlet in flow connection with the gas reservoir and extending through a boundary of the gas tight enclosure to an exterior of the gas tight enclosure;
an outlet connectable to the liquid reservoir and extending through the boundary of the gas tight enclosure, wherein the gas reservoir and the liquid reservoir are hermetically separated by an impenetrable separation wall; and
a flow meter arranged in or across the gas inlet to measure a quantity of ingress of a gaseous medium through the gas inlet in response to a withdrawal of the liquid medium from the liquid reservoir through the outlet, wherein the gas reservoir is in flow connection with atmospheric pressure via the gas inlet.

2. The measuring arrangement according to claim 1, wherein the boundary of the gas tight enclosure comprises a rigid structure.

3. The measuring arrangement according to claim 1, wherein the liquid reservoir is formed by a flexible bag filled with the liquid medium.

4. The measuring arrangement according to claim 1, wherein the liquid reservoir is formed in part by the gas tight enclosure and wherein the impenetrable separation wall comprises a flexible membrane.

5. The measuring arrangement according to claim 1, wherein the liquid reservoir is formed in part by the gas tight enclosure and wherein the impenetrable separation wall comprises a piston slidably arranged in a longitudinally extending guiding section of the gas tight enclosure.

6. The measuring arrangement according to claim 1, wherein a flow restrictor is arranged in or across the gas inlet between an inlet end of the gas inlet and the flow meter.

7. The measuring arrangement according to claim 1, wherein the flow meter comprises a differential pressure sensor.

8. The measuring arrangement according to claim 1, further comprising a controller connected to the flow meter to calculate a volume change of the liquid reservoir based on signals received from the flow meter.

9. The measuring arrangement according to claim 1, wherein the gas tight enclosure comprises at least a first part and a second part that are detachably connectable to form the interior volume.

10. The measuring arrangement according to claim 9, wherein the gas inlet is connected to the first part or is integrated into the first part and wherein the flow meter is connected to the first part.

11. The measuring arrangement according to claim 9, wherein the liquid reservoir is filled with a liquid medicament and wherein the liquid reservoir is arranged in the second part.

12. A drug delivery device comprising:
a measuring arrangement comprising:
a gas tight enclosure having an interior volume containing a gas reservoir and containing the liquid reservoir, wherein the liquid reservoir is filled with the liquid medium,
a gas inlet in flow connection with the gas reservoir and extending through a boundary of the gas tight enclosure to an exterior of the gas tight enclosure,
an outlet connectable to the liquid reservoir and extending through the boundary of the gas tight enclosure, wherein the gas reservoir and the liquid reservoir are hermetically separated by an impenetrable separation wall, and
a flow meter arranged in or across the gas inlet to measure a quantity of ingress of a gaseous medium through the gas inlet in response to a withdrawal of the liquid medium from the liquid reservoir through the outlet, wherein the gas reservoir is in flow connection with atmospheric pressure via the gas inlet; and
a delivery mechanism operably engageable with the liquid reservoir.

13. The drug delivery device according to claim 12, wherein the delivery mechanism comprises a suction pump flow-connectable with the outlet or with the liquid reservoir to withdraw the liquid medium from the liquid reservoir.

14. The drug delivery device according to claim 12, wherein the gas tight enclosure of the measuring arrangement comprises at least a first part and a second part that are detachably connectable to form the interior volume, wherein at least one of the first part and the second part forms at least a portion of the gas tight enclosure of the drug delivery device.

15. The drug delivery device according to claim 12, wherein the boundary of the gas tight enclosure comprises a rigid structure.

16. The drug delivery device according to claim 12, wherein the liquid reservoir is formed by a flexible bag filled with the liquid medium.

17. The drug delivery device according to claim 12, wherein the liquid reservoir is formed in part by the gas tight enclosure and wherein the impenetrable separation wall comprises a flexible membrane.

18. The drug delivery device according to claim 12, wherein the liquid reservoir is formed in part by the gas tight enclosure and wherein the impenetrable separation wall comprises a piston slidably arranged in a longitudinally extending guiding section of the gas tight enclosure.

19. The drug delivery device according to claim 12, wherein a flow restrictor is arranged in or across the gas inlet between an inlet end of the gas inlet and the flow meter.

20. A method of using a measuring arrangement, the measuring arrangement comprising:
- a gas tight enclosure having an interior volume containing a gas reservoir and containing a liquid reservoir, wherein the liquid reservoir is filled with a liquid medium;
- a gas inlet in flow connection with the gas reservoir and extending through a boundary of the gas tight enclosure to an exterior of the gas tight enclosure;
- an outlet connectable to the liquid reservoir and extending through the boundary of the gas tight enclosure, wherein the gas reservoir and the liquid reservoir are hermetically separated by an impenetrable separation wall; and
- a flow meter arranged in or across the gas inlet to measure a quantity of ingress of a gaseous medium through the gas inlet in response to a withdrawal of the liquid medium from the liquid reservoir through the outlet, wherein the gas reservoir is in flow connection with atmospheric pressure via the gas inlet;

the method comprising:
- withdrawing a portion of the liquid medium from the liquid reservoir thereby inducing a volume change of the liquid reservoir leading to a movement or deformation of the impenetrable separation wall enlarging a volume of the gas reservoir;
- measuring, by the flow meter, a quantity of ingress of the gaseous medium into the gas reservoir through the gas inlet; and
- deriving the volume change of the liquid reservoir based on the measured quantity of ingress of the gaseous medium into the gas reservoir.

* * * * *